United States Patent [19]
Akutsu et al.

[11] Patent Number: 5,415,784
[45] Date of Patent: May 16, 1995

[54] SAMPLE SEPARATOR HAVING IMPEDANCE INTERFACE DETECTOR

[75] Inventors: Masaki Akutsu, Tokyo; Nobukazu Takahashi, Ina, both of Japan

[73] Assignee: Olympus Optical Co., Ltd., Tokyo, Japan

[21] Appl. No.: 54,845

[22] Filed: Apr. 29, 1993

[30] Foreign Application Priority Data

May 1, 1992 [JP]  Japan .................................. 4-112604

[51] Int. Cl.⁶ ............................................ B01D 17/12
[52] U.S. Cl. ..................... 210/746; 204/406; 210/86; 210/789; 422/82.01; 422/105; 436/150
[58] Field of Search ................ 210/85, 86, 512.1, 516, 210/787, 789, 746; 422/68, 72, 82.01, 82.02, 105, 106, 107; 436/45, 63, 150, 177; 73/863.01, 863.02; 340/606; 204/406, 407

[56] References Cited
U.S. PATENT DOCUMENTS

| | | | |
|---|---|---|---|
| 4,487,836 | 12/1984 | Takayanagi et al. | 436/150 |
| 4,927,545 | 5/1990 | Roginski | 210/85 |
| 4,939,925 | 7/1990 | Sakuma et al. | 73/863.02 |
| 4,962,041 | 10/1990 | Roginski | 436/150 |

FOREIGN PATENT DOCUMENTS

| | | |
|---|---|---|
| 0210014 | 1/1987 | European Pat. Off. |
| 3909515 | 10/1989 | Germany |
| 57-90158 | 6/1982 | Japan ................. 422/82.02 |

Primary Examiner—Joseph W. Drodge
Attorney, Agent, or Firm—Frishauf, Holtz, Goodman & Woodward

[57] ABSTRACT

The sample separator including a first suction nozzle, serving also as an electrode, for extracting one of first and second components each having an impedance different from each other, a second suction nozzle, serving also as an electrode, for extracting the other component, a nozzle driving member for ascending/descending the nozzles as one unit, and an interface detecting member for detecting an interface between two components. The interface detecting member further including an impedance detector for detecting an impedance between the two nozzles serving also as the electrodes, a storing section for storing a first threshold value to detect the first component, and an operation control member for comparing the first threshold value stored in the storing member with a detected value obtained by the impedance detector, and for controlling the nozzle driving member based on a result of the comparison.

8 Claims, 5 Drawing Sheets

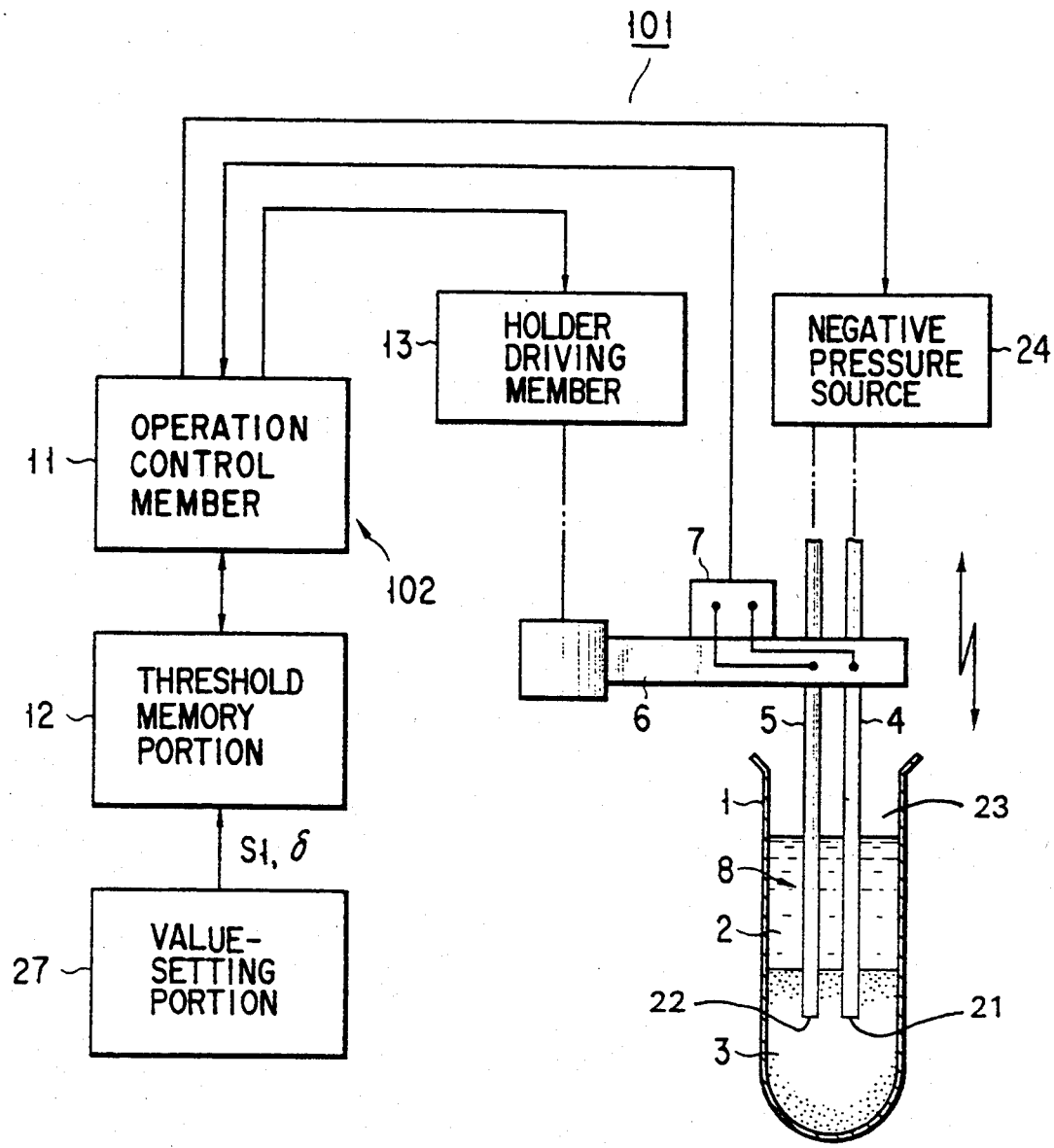
F I G. 1

SAMPLE SEPARATOR HAVING IMPEDANCE INTERFACE DETECTOR

BACKGROUND OF THE INVENTION

1. Field of the Invention

The present invention relates to a sample separating device, more specifically, a device for separating the components of a blood sample from each other.

2. Description of the Related Art

Generally, in the analysis of a blood sample, the blood sample is centrifuged, and the centrifuged components (blood plasma and blood cell, or serum and blood clot) are separately collected. A separating device of this type has an interface detector, and the interface between components adjacent to each other is detected by the interface detector.

FIG. 7 shows the main portion of the separating device. The separating device includes a plasma suction nozzle 4 and a blood cell suction nozzle 5, which are integrally set to a holder 6. Both nozzles 4 and 5 are connected to an impedance detector 7. The nozzles 4 and 5 are made of a conductive material, and serve also as electrodes. The nozzles are also connected to a suction driving source (not shown). The holder 6 is moved downward by a holder driving member (not shown).

As the holder 6 descends, both nozzles 4 and 5 approach a test tube 1, and reach a blood sample 8 in the test tube 1. While the nozzles 4 and 5 are descending, the impedance between the nozzles 4 and 5 is detected by an impedance detector 7. When the output value from the impedance detector 7 reaches a predetermined threshold value for the plasma detection, the holder 6 stops and a plasma component 2 is taken in from the plasma suction nozzle 4.

After the suction of the plasma component, the descent of the nozzles 4 and 5 is started once again. When the output value from the impedance detector 7 reaches a predetermined threshold value for the blood cell detection, the holder 6 stops and a cell component 3 is taken in from the cell suction nozzle 5.

For a simple explanation, the holder driving means for the holder 6 and the comparator are not shown in FIG. 7.

FIG. 8 is a diagram showing a typical example of the relationship between a nozzle position and an output from the impedance detector 7. As the tip end of each of the nozzles 4 and 5 proceeds through the air, the plasma component, and the blood cell, the impedance significantly varies, as shown in the figure. The impedance is at the highest level when the tip ends of the nozzles 4 and 5 are both in the air, and is at the lowest level when in the plasma component 2. When the tips of the nozzles 4 and 5 are located in the blood cell component 3, the impedance is somewhere between the two levels. In the figure, X and Y represent standard plasma impedance and blood cell impedance, respectively.

Before the separation of the components, a threshold value, $S_1$, for plasma detection and a threshold value, $S_2$, for blood cell detection are determined. The value $S_1$ is set lower than the value $S_2$. The impedance having a value of $S_1$ indicates that the plasma suction nozzle 4 has reached the plasma component 2. When this indication is detected, the plasma component 2 is taken in. The nozzles 4 and 5 further descend and when the impedance exceeds the value $S_2$, which indicates that the blood cell suction nozzle 5 has reached the blood cell component 3, the cell component 3 is taken in.

It should be noted here that the variation of the impedance is not always constant for any type of blood samples, but each sample has its own variation characteristic of impedance. If the threshold values $S_1$ and $S_2$ are set at a constant for any blood samples regardless of the unique variation characteristic of each sample, it is difficult to accurately detect the interface between a plasma component 2 and a blood cell component 3.

For example, when a detected blood cell impedance $Y_1$ is much lower than a standard value (indicated by dot line $9a$), and is even lower than the threshold value $S_2$ for a blood cell components, the blood cell component 3 cannot be detected from the $S_2$ value.

As shown in FIG. 9, a blood cell component 3 having such a low impedance can be detected by setting the $S_2$ value lower than $Y_1$. However, in order to detect the plasma 2, the $S_1$ value must be set even lower than $S_2$. If the $S_1$ value is simply set at a low level, $S_1$ may be lower than $X_1$. Therefore, in the case where the detected plasma impedance $X_1$ is much higher than the standard plasma impedance X (dot line $9b$), the plasma component cannot be detected.

In general, plasma suction nozzles 4 and 5, which are mass-produced, do not have exactly the same impedance, but the impedance varies from one to another. The impedance of each nozzle also varies with time (i.e. aging of nozzles). Other than the unique characteristic of each blood sample, the above factors cause an increase in the plasma impedance $X_1$.

The present invention has been proposed in consideration of the above drawbacks of the conventional technique, and the purpose of the invention is to provide a sample separator capable of accurately detecting the interface between components adjacent to each other regardless of the difference between samples in characteristics.

SUMMARY OF THE INVENTION

According to the present invention, there is provided a sample separator comprising: a first suction nozzle, serving also as an electrode, for extracting one of first and second components each having an impedance different from each other; a second suction nozzle, serving also as an electrode, for extracting the other component; a nozzle driving member for ascending/descending the nozzles as one unit; and an interface detecting member for detecting an interface between two components;

the interface detecting member further including an impedance detector for detecting an impedance between the two nozzles serving also as the electrodes, a storing section for storing a first threshold value to detect the first component, and an operation control member for comparing the first threshold value stored in the storing member with a detected value obtained by the impedance detector, and for controlling the nozzle driving member based on a result of the comparison.

With the structure described above, the interface between two components can be accurately detected regardless of a variety of the characteristics of blood samples.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a diagram showing the first embodiment of the present invention;

DETAILED DESCRIPTION OF THE PREFERRED EMBODIMENTS

Figure 2:
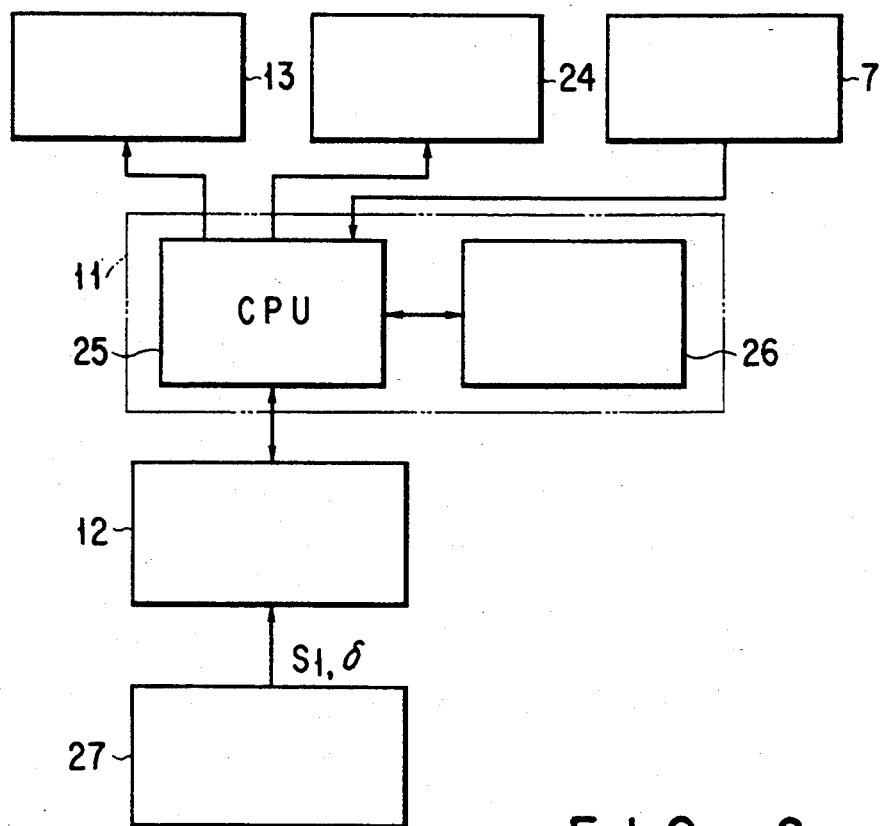
FIG. 2 is a block diagram showing a structure of the operation control member and the periphery thereof.

Embodiments of the present invention will now be described with reference to the accompanying drawings. Those elements of the embodiments which are similar to those of the prior art device will be designated by the same reference numerals.

FIG. 1 shows the first embodiment of the present invention, and depicts a sample separator 101, and an interface detecting member 102 set in the sample separator. The sample separator 101 separately extracts two components (a plasma component 2 and a blood cell component 3) of a blood sample 8, which was centrifuged. The interface detecting member 102 detects the interface between the plasma component 2 and the blood cell component 3.

The sample separator 101 includes a pair of nozzles, a plasma suction nozzle 4 serving as a first suction nozzle, and a blood cell suction nozzle 5 serving as a second suction nozzle. The nozzles 4 and 5 have a hollow structure, and are fixed to a holder 6. The holder 6 is connected to a holder driving member 13, serving as a nozzle driving member, which is further connected to an operation control member 11 (described later). The holder driving member 13 moves the holder up or down, or stops in accordance with an instruction from the operation control member 11.

The nozzles 4 and 5 both project vertically downward from the holder 6, and are arranged in parallel with each other. The distance between the nozzles 4 and 5 is set such that they enter into a test tube 1 at the same time. Further, the tip ends 21 and 22 of the nozzles 4 and 5 are virtually level with each other.

The nozzles 4 and 5 descends or ascends along with the holder 6 as one unit. As the holder descends, the nozzles 4 and 5 gradually enter into the test tube 1, and the tip ends 21 and 22 proceed through the air section 23, the plasma component 2, to the blood cell component 3. The positions of the tip ends 21 and 22 are adjusted by the holder driving member 13. FIG. 1 shows a case where the tip ends of the nozzles 4 and 5 are located in the blood cell component 3.

The nozzles 4 and 5 are connected to a negative pressure source 24, which is also connected to the operation control member 11. The negative pressure source 24 is driven in accordance with an instruction from the operation control member 11, and each of the nozzles 4 and 5 independently performs a suction operation as driven by the negative pressure source 24.

Each of the nozzles 4 and 5 are made of a conductive material, and therefore serves also as an electrode. The nozzles 4 and 5 are connected to the impedance detector 7, which is set in the holder 6. The impedance detector 7 is connected to the operation control member 11 so as to detect an impedance between the nozzles 4 and 5, and output the result of the detection to the operation control member 11.

As shown in FIG. 2, the operation control member 11 includes a CPU 25 and a comparison operation member 26. Connected to the operation control member 11, connected are the impedance detector 7, the holder driving member 13, the negative pressure source 24, and a threshold value storing member 12 serving as a memory. A value-setting member 27 is connected to the threshold value storing member 12. As the threshold value storing member 12, general types of memories can be used. As the value-setting member 27, general types of keyboards, or the like, can be used. The operation control member 11 may include the threshold value storing member 12.

Figure 8:
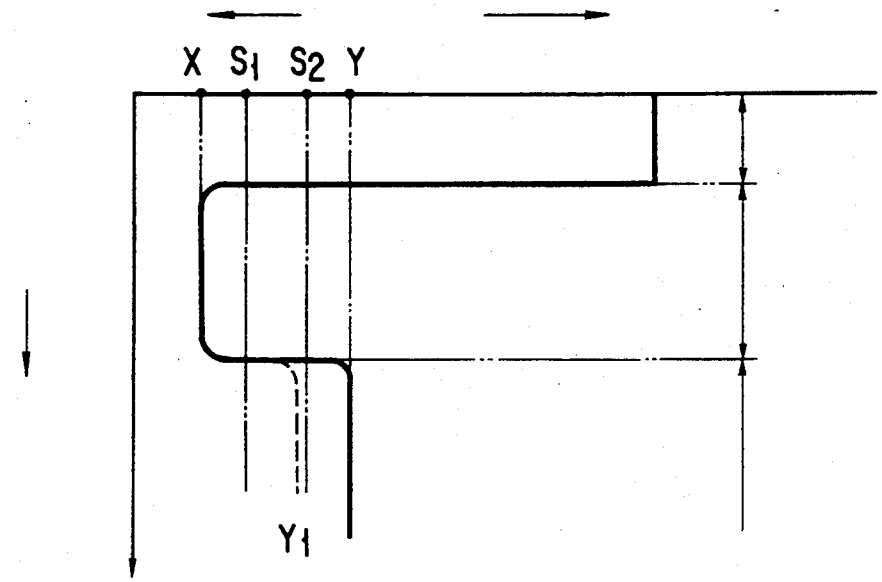
FIG. 8 is a graph showing a typical relationship between a descending position of the nozzle and an impedance.
Figure 9:
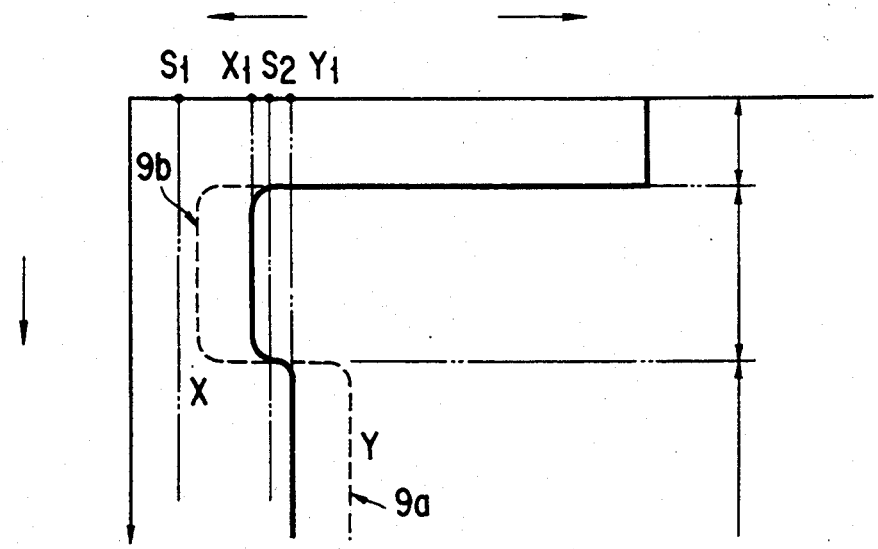
FIG. 9 is a graph showing a variation of the impedance in the case where the plasma impedance is much higher, and the blood cell impedance is much lower than a standard case.

In the threshold value storing member 12, a threshold value, $S_1$, for plasma detection is stored by the value-setting member 27. A threshold value $S_1$ is determined based on a standard plasma impedance X and a standard blood cell impedance Y shown in FIG. 3. More specifically, the value $S_1$ is set sufficiently higher than the plasma impedance X, and slightly lower than the cell impedance Y. Further, the value $S_1$ of the embodiment is sufficiently higher than the value $S_1$ of the conventional device (shown in FIG. 8).

A threshold value, $S_2$, for blood cell detection determined based on the result of the detection by the impedance detector 7. More specifically, the operation control member 11 recognizes a plasma impedance $X_1$ (minimum impedance) of a sample 8 from the output signal from the impedance detector 7, and determines a value $S_2$ by adding a predetermined amount $\delta$ to the impedance $X_1$. The addition value $\delta$ is small with respect to the difference between the plasma impedance $X_1$ (detected value) and the blood cell impedance Y (reference value). Consequently, the value $S_2$ is slightly higher than a detected plasma impedance $X_1$. The value $S_2$ varies in accordance with the plasma impedance $X_1$ of a sample 8. An addition value $\delta$ is determined by use of the value-setting member 27.

In the operation control member 11, the result of a detection by the impedance detector 7, a plasma detection threshold value $S_1$, and a blood cell detection threshold value $S_2$ are compared with each other. The operation control member 11 controls the holder drive member 13 and the negative pressure source 24 in accordance with the results of the comparison.

The operation of the sample separating apparatus 101 having the above-described structure will be described.

When an operation of the apparatus 101 is started, the holder drive member 13 lowers the holder 6. At the same time, a detection signal from the impedance detector 7 is input to the operation control member 11, where the detection signal and the plasma detection threshold value $S_1$ are compared with each other.

Figure 3:
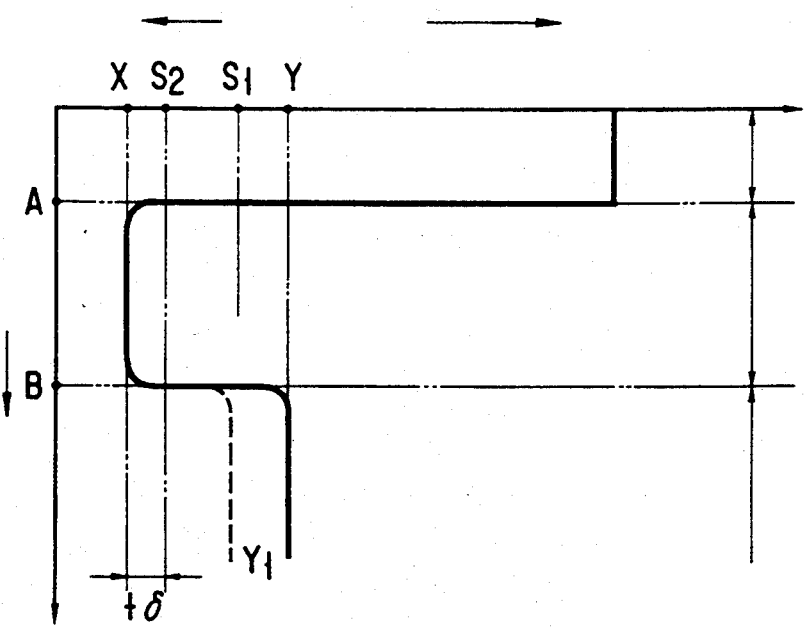
FIG. 3 is a diagram designed to explain a threshold value.
Figure 4:
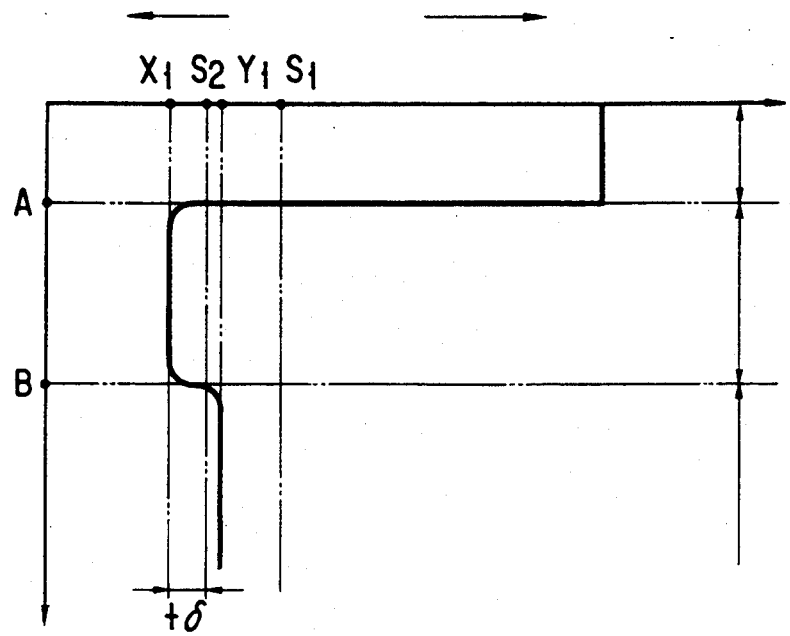
FIG. 4 is a graph showing a variation of the impedance in the case where the plasma impedance is much higher, and the blood cell impedance is much lower than a standard case.

The impedance decreases noticeably when the tip ends 21 and 22 of a pair of nozzles 4 and 5 are immersed in the plasma component 2. In FIG. 3, symbol A indicates the level of the tip ends of the nozzles when the impedance significantly drops, and the tip end level A is at the interface between the air component 23 and the plasma component 2.

When the impedance decreases to $S_1$ or lower, the holder drive member 13 stops lowering the holder 6 in accordance with an instruction from the operation control member 11. After that, the negative pressure source 24 is driven such that the plasma suction nozzle 4 starts to extract the plasma component 2. The minimum impedance at this point, that is, a plasma impedance $X_1$, is stored in the threshold memory member 12 via the operation member 11.

After extracting a predetermined amount of the plasma component 2, the holder drive member 13 once again lowers the holder 6. While the holder is descending, the impedance is continuously detected by the impedance detector 7. when the tip ends 21 and 22 of the nozzles 4 and 5 reach the blood cell component 3 (nozzle level B in FIG. 2), the impedance rapidly increases. When the impedance increases and gets a predetermined amount ($\delta$) higher than the plasma impedance $X_1$ previously stored, the operation control member 11 outputs an instruction to the holder drive member 13 so as to stop the holder 6. Then, the negative pressure source 24 is driven such that the cell suction nozzle 5 starts to extract the blood cell component 3. The blood cell threshold value $S_2$ is represented by ($X_1+\delta$).

The result of the detection obtained by the impedance detector 7 is influenced by the accuracy of impedance detector 7, the impedance of the each of the nozzles 4 and 5, which may vary from one another, and the like. The $S_1$ and $\delta$ values that are optimum for detecting an interface should be determined in consideration of the above factors.

In the sample separator 101 having the above described structure, a plasma detection threshold value $S_1$ is determined based on a typical plasma impedance, and the threshold $S_1$ is set considerably larger than the typical plasma impedance X. Thus, if the detected plasma impedance X increases due to the impedance of each of the nozzles 4 and 5 which may vary from one to another, and a characteristic change of each of the nozzles 4 and 5 with time, the plasma component 2 can be accurately detected.

The blood cell detection threshold value $S_2$ is set at ($X_1+\delta$) in accordance with the plasma impedance X detected each time. Consequently, the blood cell component 3 can be detected even if the blood cell impedance $Y_1$ is significantly lower than a typical blood cell impedance Y.

With the above-described arrangement, the interface between the plasma component 2 and the blood cell component 3 is accurately detected regardless of characteristic differences between blood samples. Even if the difference between the plasma impedance $X_1$ and the blood cell impedance $Y_1$ in a sample 8, is small, the interface therebetween can be detected.

Regarding a blood sample centrifuged into a serum plasma component and a blood clot, the detection of the interface between the components can be carried out in a similar manner.

The present invention can be modified into a variety of versions as long as the essence of the invention remains.

Figure 5:
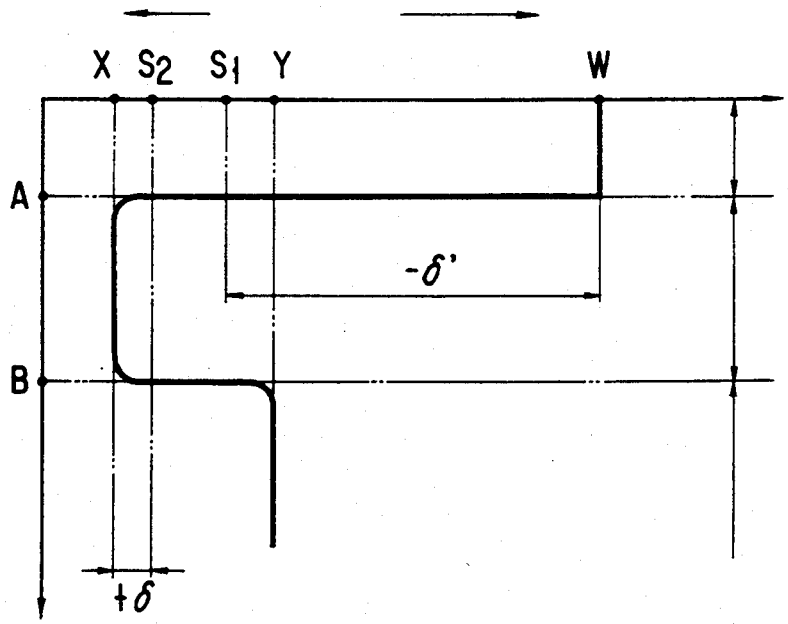
FIG. 5 is a graph designed to explain the second embodiment of the present invention.

FIG. 5 shows the main section of the second embodiment of the present invention. A great portion of this embodiment is common to the first embodiment, and therefore an apparatus similar to the first embodiment can be used. The common part is omitted from the figure.

In this embodiment, a plasma detection threshold value $S_1$ is determined based on an air impedance W. Before lowering of nozzles 4 and 5, the impedance between the nozzles is detected, and the detected value is stored in a memory portion 12 as an air impedance W.

In an operation control member 11, a value is obtained by subtracting a predetermined amount $\delta'$ from the air impedance W, and the value ($W-\delta'$) is recognized as a plasma detection threshold value $S_1$. The value $S_1$ is stored in the threshold memory portion 12, and compared with a value detected by the impedance detector 7. The subtraction value $\delta'$ is input to a threshold memory portion 12 along with the addition value $\delta$ by use of a value-setting member 27 before extraction of the plasma component 2. Thus, an optimum value $\delta'$ is determined in a similar way to $S_1$ or $\delta$ of the first embodiment.

Also in the second embodiment, the interface between the plasma component 2 and the blood cell component 3 can be accurately detected regardless of the characteristic difference between blood samples 8.

Figure 6:
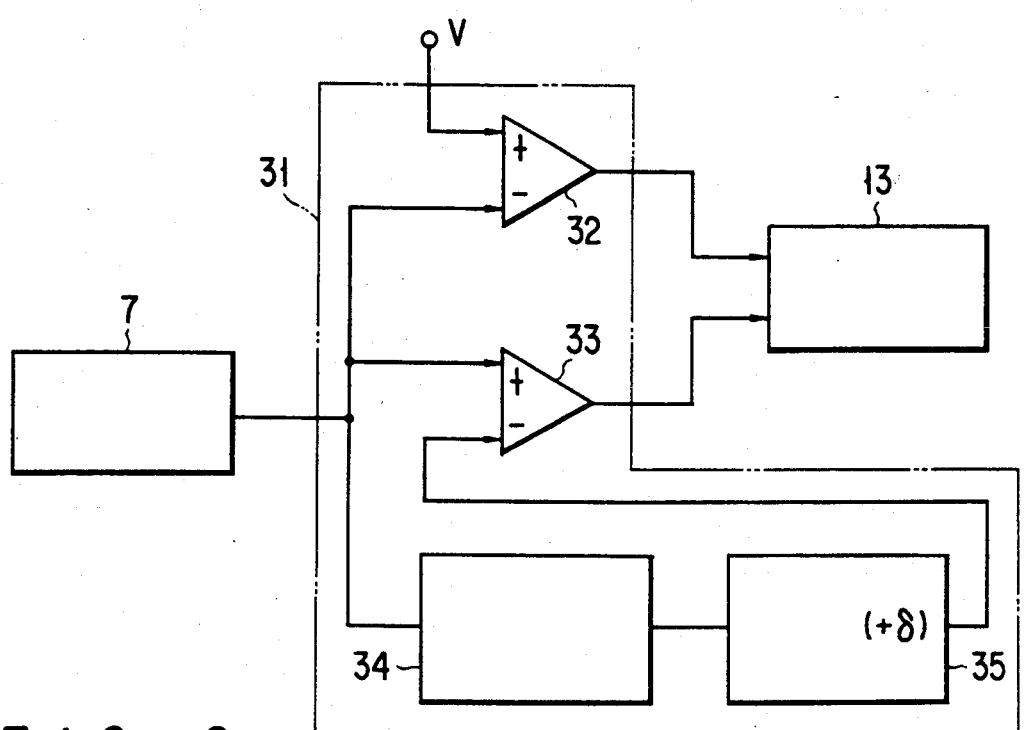
FIG. 6 is a block diagram showing a structure of the operation control member and the periphery thereof in the third embodiment of the invention.
Figure 7:
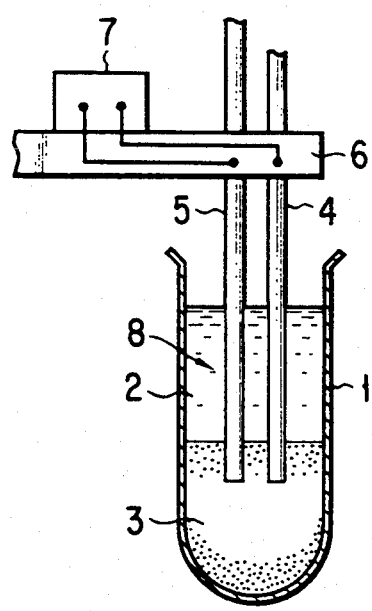
FIG. 7 is a diagram showing a conventional separator.

FIG. 6 shows the third embodiment of the present invention. In the first embodiment, the operation control member 11 includes electronic parts, in each of which circuits elements are integrated, such as CPU 25, memory 12, and the like, whereas in this embodiment, an operation control member 31 is an electronic circuit in which comparators 32 and 33 are employed. The operation control member 31 includes the first and second comparators 32 and 33, a negative peak-hold circuit 34, and an adder 35. Supplied the first comparator 32 are a reference voltage V, and an output signal from an impedance detector 7, whereas to the second comparator 33 are input a signal from the impedance detector 7, and an addition result from the adder 3. The adder 35 adds a predetermined value $\delta$ to a value held by the negative peak-hold circuit 34.

The obtained output value from the impedance detector 7 varies as the holder 6 descends. The detected signal from the impedance detector 7 is input to the first comparator 32, and compared with the reference voltage V. The reference voltage V represents a plasma detection threshold value $S_1$. when the detected signal decreases to the level of the reference voltage V or lower, a signal is output to the holder drive member 13 so as to stop the holder 6. Thus, extraction of the plasma component is started. The minimum impedance at this point is held by the negative peak-hold circuit 34 as a plasma impedance $X_1$.

After extracting a predetermined amount of the plasma component 2, the holder 6 is further lowered, and while the holder being lowered, the impedance between the nozzles 4 and 5 is continuously detected. The impedance values detected are successively input to the second comparator 33 along with the addition results from the adder 35. The adder 35 adds a predetermined value $\delta$ to the plasma impedance $X_1$, and the addition result $(X_1+\delta)$ is output to the negative input terminal of the second comparator 33. The second comparator 33 compares the result detected by the impedance detector 7 and the result $(X_1+\delta)$ obtained by the adder 35. If an impedance value detected by the impedance detector 7 is $(X_1+\delta)$ or higher, the holder drive member 13 stops the holder 6, and extraction of the blood cell sample 3 is carried out.

In this embodiment, the interface between the plasma component 2 and the blood cell component 3 is accurately detected regardless of the characteristic difference between blood samples as in the other embodiments described above.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A sampling apparatus for separately suctioning first and second components of a sample, which have different impedances, comprising:
    a first suction nozzle having a suction portion for sucking one of said first and second components, and an electrode portion;
    a second suction nozzle having a suction portion for sucking the other of said first and second components, and an electrode portion;
    a nozzle driving unit for raising/lowering said nozzles together;
    an impedance detector coupled to the electrode portions of said nozzles for detecting an impedance therebetween at a plurality of positions as said nozzle driving unit lowers said nozzles;
    storing means for storing a value which is higher than a standard impedance of said first component and lower than a standard impedance of said second component, as a first threshold value;
    setting means for setting a value obtained by means comprising an adder, electronically coupled to said storing means, for adding a predetermined value to an impedance of said first component of said sample, detected by said impedance detector, as a second threshold value; and
    an operation control member for initially comparing impedances detected by said impedance detector, when said first and second nozzles are lowered, with said first threshold value, and for allowing said first suction nozzle to suck said first component when one of said detected impedances is at said first threshold value or lower, and then comparing impedances detected by said impedance detector with said second threshold value as said first and second nozzles continue to descend for allowing said second suction nozzle to suck said second component when one of said detected impedances is at said second threshold value or higher.

2. A sample separator according to claim 1, wherein the setting means sets the second threshold value such that it is lower than the first threshold value.

3. A sample separator according to claim 1, wherein said storing means stores the first threshold value at a value determined in accordance with an air section impedance.

4. A sample separator according to claim 3, wherein the operation control member determines the first threshold value by subtracting a predetermined subtraction value from an air impedance.

5. A sample separator according to claim 1, wherein the operation control member includes a negative peak-hold circuit for holding a negative peak of detected values obtained by the impedance detector, said adder for adding a predetermined value to the negative peak value held by the negative peak-hold value, and a comparator which compares the detected value obtained by the impedance detector, and the addition result of the adder, and outputs a comparison result to the nozzle driving unit for detection of the second component.

6. A sample separator according to claim 1, wherein the operation control member includes a negative peak-hold circuit for holding a negative peak of detected values obtained by the impedance detector, said adder for adding a predetermined value to the negative peak value held by the negative peak-hold value, a first comparator comparing the first threshold value with the detected value obtained by the impedance detector, and outputting a comparison result to the nozzle driving unit for detection of the first component, and a second comparator comparing the detected value obtained by the impedance detector, and the addition result of the adder, and outputting a comparison result to the nozzle driving unit for detection of the second component.

7. A sampling method of separately suctioning first and second components of a sample, which have different impedances, comprising the steps of:
    storing a value which is higher than a standard impedance of said first component and lower than a standard impedance of said second component, as a first threshold value;
    lowering two suction nozzles each having a suction nozzle portion, and an electrode portion for detecting an impedance of said sample;
    continuing detection of an impedance of said sample at a plurality of nozzle positions as said nozzles are being lowered;
    comparing an impedance detected between the electrode portions of said nozzles with said first threshold value;
    setting a value obtained by using an adder, electronically coupled to means utilized for said storing, by adding a predetermined value to an impedance of said first component of said sample, as a second threshold value;
    allowing one of said nozzles to suck said first component when an impedance detected by said nozzles is at said first threshold value or lower; and
    allowing the other of said nozzles to suck said second component when said impedance detected after suction of said first component has occurred is at said second threshold value or higher.

8. A sampling method according to claim 7, wherein the step of storing said first threshold value further comprises a step of detecting an impedance of an air section before said nozzles are lowered into the sample.

* * * * *